US011534551B2

United States Patent
Ferreri et al.

(10) Patent No.: US 11,534,551 B2
(45) Date of Patent: Dec. 27, 2022

(54) CLIP SYRINGE

(71) Applicant: Becton, Dickinson and Company, Franklin Lakes, NJ (US)

(72) Inventors: Suzanne Ferreri, Ridgewood, NJ (US); Adam Zerda, Cary, NC (US); James J. Kennedy, III, Mont Vernon, NH (US); Morgan Carlson, Nashua, NH (US); Darrin Manke, North Andover, MA (US); Lee Panecki, San Francisco, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 715 days.

(21) Appl. No.: 16/033,683

(22) Filed: Jul. 12, 2018

(65) Prior Publication Data

US 2018/0318512 A1 Nov. 8, 2018

Related U.S. Application Data

(63) Continuation of application No. 13/925,172, filed on Jun. 24, 2013, now Pat. No. 10,039,884.
(Continued)

(51) Int. Cl.
*A61M 5/24* (2006.01)
*A61M 5/28* (2006.01)
(Continued)

(52) U.S. Cl.
CPC ........ *A61M 5/3129* (2013.01); *A61M 5/2425* (2013.01); *A61M 5/282* (2013.01);
(Continued)

(58) Field of Classification Search
CPC ........ A61M 11/008; A61M 2005/3246; A61M 3/0262; A61M 5/282; B65D 35/40;
(Continued)

(56) References Cited

U.S. PATENT DOCUMENTS 3,203,596 A * 8/1965 Davidson ............... B65D 35/28
222/105
3,281,016 A * 10/1966 Thompson ............. B65D 35/28
222/105
(Continued)

FOREIGN PATENT DOCUMENTS

DE 19545838 A1 6/1997
DE 10032937 A1 1/2001
(Continued)

OTHER PUBLICATIONS

PCT International Search Report and Written Opinion in PCT/US2013/047867, dated Dec. 20, 2013, 14 pages.

*Primary Examiner* — Bhisma Mehta
*Assistant Examiner* — William R Frehe
(74) *Attorney, Agent, or Firm* — Servilla Whitney LLC

(57) ABSTRACT

A single use pre-filled delivery device is disclosed having a deformable container including a side wall having an inside surface defining a chamber for retaining fluid, a clip element, and a locking element. The deformable container further includes a closed proximal end and an open distal end including a male luer tip having a passageway therethrough providing fluid communication with the chamber. The male luer tip may be removably connectable to a female luer connection of a vascular access device. The clip element includes a distal end, proximal end, and a pivot located between the distal end and the proximal end of the clip element for collapsing the deformable container to drive fluid out of the chamber by movement of the proximal end towards the distal end. The pivot may be a hinge, which may be in the form of a living hinge. The deformable container may be attached to the clip element. The locking element may be disposed on the clip element. A method of administering a fluid to a vascular access device using a single use
(Continued)

pre-filled delivery device as described herein is also disclosed.

10 Claims, 11 Drawing Sheets

Related U.S. Application Data

(60) Provisional application No. 61/664,443, filed on Jun. 26, 2012.

(51) Int. Cl.
  *A61M 5/31* (2006.01)
  *A61M 25/00* (2006.01)
  *B65D 35/28* (2006.01)

(52) U.S. Cl.
  CPC ............. *B65D 35/28* (2013.01); *A61M 25/00* (2013.01); *A61M 2025/0019* (2013.01)

(58) Field of Classification Search
  CPC ...... B65D 35/00; B65D 35/28; B65D 35/247; B65D 45/22; B65D 45/16; B65D 43/16; B65D 2251/1016; F16L 23/10
  USPC ........ 604/212, 122–125; 215/273, 280, 287; 220/315, 324, 326, 810, 833; 24/285, 24/455
  See application file for complete search history.

(56) References Cited

U.S. PATENT DOCUMENTS

| | | | | |
|---|---|---|---|---|
| 3,675,822 A | * | 7/1972 | Casali | B65D 35/28 222/103 |
| 3,768,699 A | * | 10/1973 | Robe, Jr. | B65D 35/28 222/103 |
| 4,411,656 A | * | 10/1983 | Cornett, III | B65D 1/32 604/212 |
| 4,581,021 A | * | 4/1986 | Landau | A61M 5/2425 604/187 |
| 4,645,486 A | | 2/1987 | Beal et al. | |
| 4,674,655 A | | 6/1987 | Löfgrer et al. | |
| 4,692,157 A | * | 9/1987 | Landau | A61M 5/2425 604/214 |
| 5,217,144 A | * | 6/1993 | Santefort | B65D 35/28 222/103 |
| 5,322,194 A | * | 6/1994 | Roberts | B65D 35/28 222/105 |
| 5,323,932 A | * | 6/1994 | Bauman | B65D 35/28 222/105 |
| 5,810,783 A | * | 9/1998 | Claro | A61M 5/148 604/199 |
| 5,890,625 A | | 4/1999 | De Laforcade | |
| 5,920,967 A | * | 7/1999 | Souza | B65D 35/28 222/103 |
| 6,780,171 B2 | | 8/2004 | Gabel et al. | |
| 7,243,893 B2 | * | 7/2007 | Sobue | A61J 1/16 248/459 |
| 8,033,428 B1 | * | 10/2011 | McEwin | A47K 1/09 222/93 |
| 8,747,007 B2 | * | 6/2014 | Krcma | A21C 15/005 401/160 |
| 2006/0043108 A1 | * | 3/2006 | Burrell | B65D 35/28 222/103 |
| 2007/0045340 A1 | | 3/2007 | Harper | |
| 2008/0073372 A1 | | 3/2008 | Keller | |
| 2008/0177246 A1 | | 7/2008 | Sullivan et al. | |

FOREIGN PATENT DOCUMENTS

| | | |
|---|---|---|
| JP | S49113495 U | 9/1974 |
| JP | 2002017851 A | 1/2002 |
| WO | 94/22509 A1 | 10/1994 |
| WO | 95/13839 A1 | 5/1995 |
| WO | 2006/019397 A2 | 2/2006 |
| WO | 2011/026049 A2 | 3/2011 |
| WO | 2011/026050 A2 | 3/2011 |
| WO | 2011/094025 A1 | 8/2011 |
| WO | 2012/052503 A2 | 4/2012 |

* cited by examiner

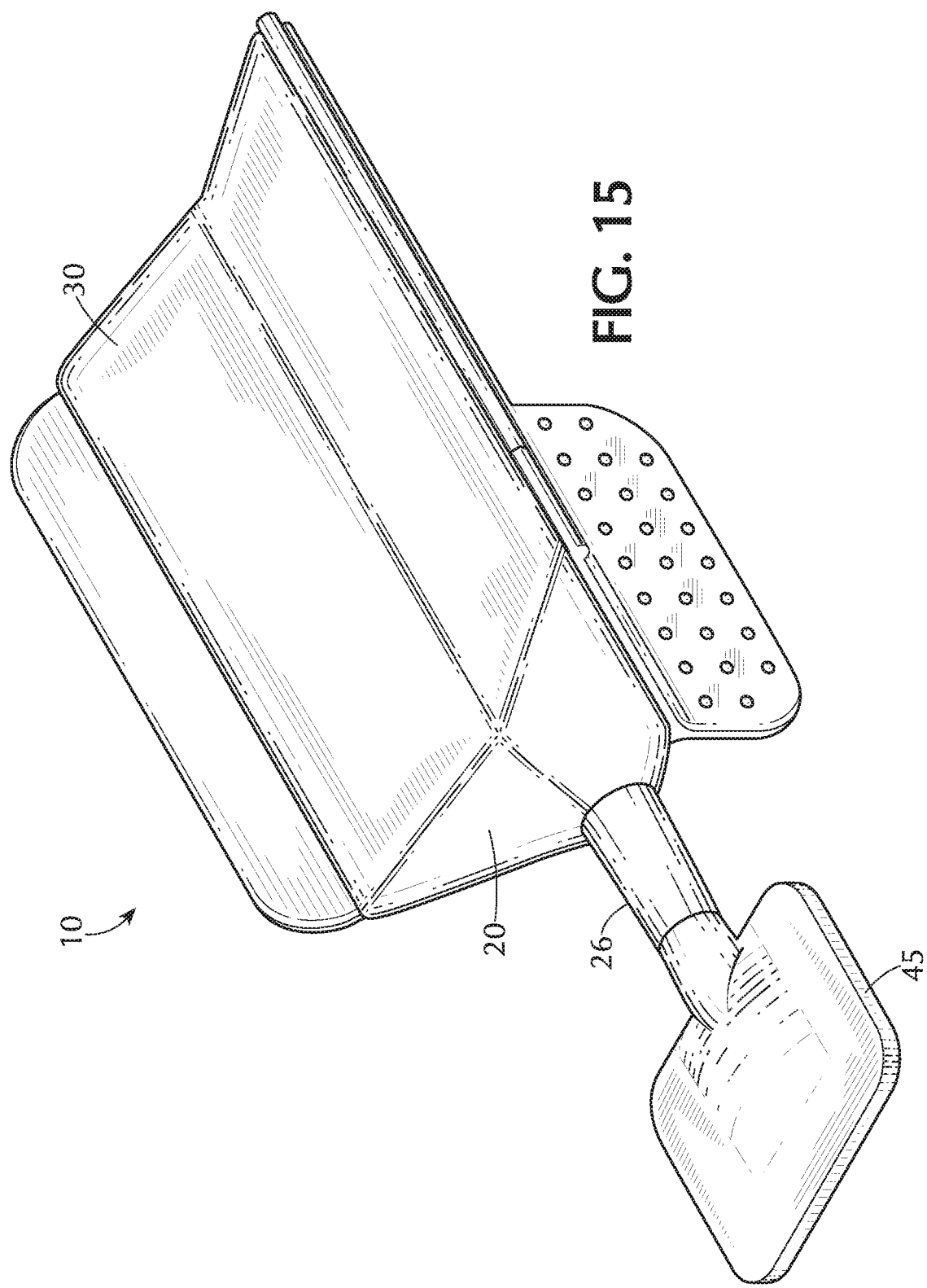

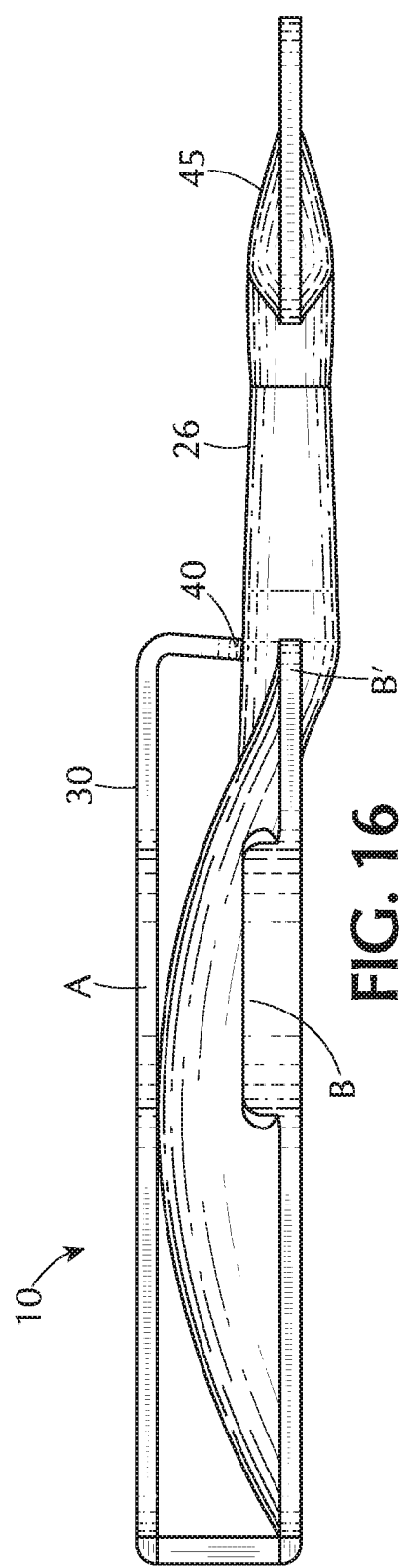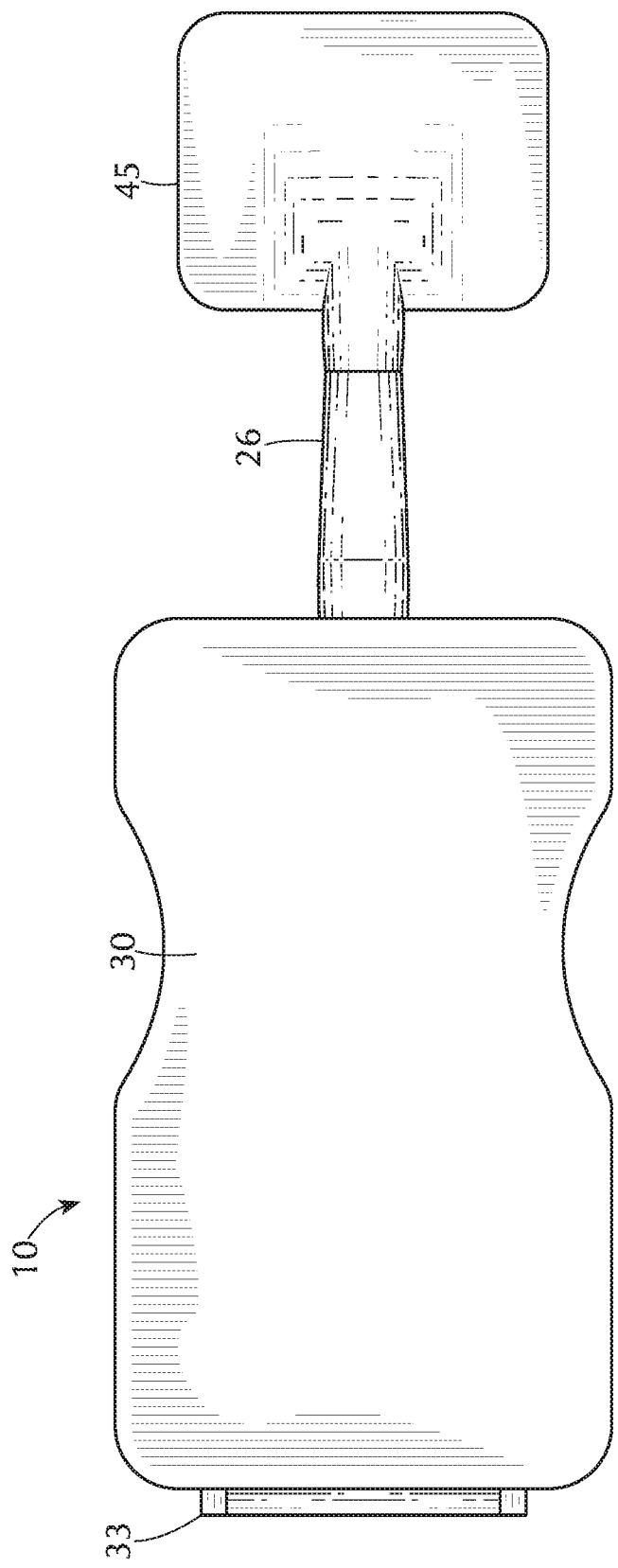

CLIP SYRINGE

CROSS-REFERENCE TO RELATED APPLICATIONS

This application is a continuation of U.S. patent application Ser. No. 13/925,172, filed Jun. 24, 2013, which claims priority under 35 U.S.C. § 119(e) to U.S. Provisional Application No. 61/664,443, filed Jun. 26, 2012, the disclosures of which are incorporated herein by reference in their entirety.

TECHNICAL FIELD

An aspect of the invention relates generally to a single use pre-filled delivery device having a deformable container including a side wall having an inside surface defining a chamber for retaining fluid, a closed proximal end and an open distal end including a male luer tip having a passageway therethrough providing fluid communication with said chamber; said male luer tip removably connectable to a female luer connection of a vascular access device; and a clip element for collapsing the deformable container having a distal end and proximal end comprising a pivot located between the distal end and the proximal end for driving fluid out of said chamber by movement of the proximal end towards the distal end, the clip element comprising a distal portion and a proximal portion, said deformable container being attached to the clip element; and a locking element disposed on the clip element. Another aspect of the invention relates generally to a method of flushing or administering a fluid using the single use pre-filled delivery device described herein.

BACKGROUND

Vascular access devices (VAD) used to access a patient's vascular space without puncture using a hypodermic needle. Vascular Access Devices (VADs) include intravenous catheters, syringes, extension sets, stop cocks, tubing, high pressure extension tubing, and needleless access devices. These devices are used in patients where frequent access is required to the vascular space for delivery of treatment and withdraw of fluids. Indwelling vascular access devices are susceptible to infection and occlusion, requiring continued preventive maintenance. To ensure VADs are used properly and do not become occluded, standards of practice have been developed to maintain the indwelling VAD. These standards include a cleaning procedure, which is commonly referred to as a flush procedure. One form of VAD maintenance is a continuous saline dip where which a saline bag is connected to the VAD and provides continuous flow of saline solution to the patient through the VAD. This approach may put the patient at risk by delivering excess fluid to the vascular space.

An alternative method for vascular device maintenance, known as flushing, involves intermittent delivery of saline thru the VAD using a hypodermic syringe. One way to deliver intermittent saline to the VAD is to fill a hypodermic syringe fitted with a needle from a saline vial or ampoule. The filled syringe is then connected to the VAD and the saline is then flushed thru the VAD into the patient. Use of pre-filled saline flush syringes to deliver saline flush to VAD's offers improved safety and efficiency over manually filled hypodermic syringes.

It is important in the flush procedure not to draw blood back into the catheter where it can clot and seal the catheter, commonly referred to as "reflux". In order to prevent blood reflux into the catheter the user is encouraged to maintain a positive pressure in the line during the flush procedure. This may involve clamping the IV line and withdrawing the syringe and cannula from the LV. port while still applying pressure to the syringe plunger rod during the flush procedure. When using a conventional syringe with an elastomeric stopper, the stopper is often compressed when it contacts the distal end of the syringe barrel at the completion of the flush procedure. When a user relieves the pressure to the plunger after the flush procedure is completed, the stopper will expand back to its normal size thereby withdrawing liquid from the catheter into the syringe barrel. This is undesirable, since it can cause blood to enter the catheter at the catheter distal end (reflux) where it will remain stationary until the next time the VAD is used.

Although a wide variety of catheters and I.V. ports can be adequately flushed using currently available syringe assemblies, as flushing practices change from continuous IV drip to intermittent flushing, there is a need for a new sterile, single use, pre-filled delivery device for maintenance of VAD's.

SUMMARY

Embodiments of the present invention are directed to a single use pre-filled delivery device having a deformable container, including a side wall having an inside surface defining a chamber for retaining fluid; a clip element; and a locking element. The deformable container further includes a closed proximal end and an open distal end including a male luer tip having a passageway therethrough providing fluid communication with the chamber. The deformable container may be made of thermoplastic elastomers, polyolefin, polyester or other injection moldable or formable resin. Thermoplastic elastomers include, but are not limited to, polypropylene, polyethylene and the like. The male luer tip may be removably connectable to a female luer connection of a vascular access device. The clip element includes a distal end, proximal end, and a pivot located between the distal end and the proximal end of the clip element for collapsing the deformable container to drive fluid out of the chamber by movement of the proximal end towards the distal end. In one or more embodiments, the pivot may be a hinge, which may be in the form of a living hinge. The deformable container may be attached to the clip element. The locking element may be disposed on the clip element.

In one or more embodiments, the single use pre-filled delivery device further includes a tip cap that is releasably connected to the male luer tip of the deformable container for sealing the passageway.

In one or more embodiments, the vascular access device is a syringe, extension set, intravenous set, stop cock, tubing, high pressure extension tubing, or needleless connector.

In one or more embodiments, the single use pre-filled delivery device further includes a pre-selected amount of fluid in the chamber. The pre-selected amount of fluid in the chamber may be from 0.5 ml to 10 ml. In one or more embodiments, the fluid may include a medicament, drug or flush solution, such as saline solution.

The locking element of the present invention minimizes, limits or prevents reflux of solution in the passageway. The locking element also provides confirmation to the user of solution delivery by providing feedback to the user to confirm delivery of a desired volume of fluid from the chamber. The feedback may be tactile, visual or audible. In one or more embodiments, the locking element includes at least one protrusion and at least one corresponding cavity. In one or more embodiments, the at least one protrusion is disposed on the proximal end of the clip element and the corresponding cavity is disposed on the distal end of the clip element. In another embodiment, the at least one protrusion is disposed on the distal end of the clip element and the at least one corresponding cavity is disposed on the proximal end of the clip element. The locking element is arranged to be manually activated by a user after the protrusion engages to the corresponding cavity after the fluid has been expelled from the deformable container. In an alternate embodiment of the present invention, the locking element includes detents. In yet another alternate embodiment of the present invention, the locking element includes a racheting mechanism having a plurality of teeth and a catch. In one embodiment, the catch is disposed on the proximal end of the clip element and the plurality of teeth is disposed on the distal end of the clip element. In another embodiment, the catch is disposed on the distal end of the clip element and the plurality of teeth is disposed on the proximal end of the clip element. The locking element is arranged to be manually activated by a user after the catch engages to one or more of the plurality of teeth.

In yet another alternate embodiment of the present invention, the locking element includes a snap fit element to connect the distal end of the clip element to the proximal end of the clip element upon the release.

In one embodiment, the pivot is positioned on the proximal end of the deformable container. In another embodiment, the pivot is positioned on the distal end of the deformable container. The pivot may be oriented in a perpendicular position with respect to the distal end of the deformable container.

In one or more embodiments, the clip element further includes at least one protrusion for removing one or more air bubbles from the delivery device and controlling the delivery of fluid from the delivery device.

In an alternate embodiment of the present invention, a single use pre-filled delivery device having a deformable container includes a side wall having an inside surface defining a chamber for retaining fluid, a closed proximal end and an open distal end including a male luer tip having a passageway therethrough providing fluid communication with said chamber, a three-fold clip element and a locking element. The male luer tip is removably connectable to a female luer connection of a vascular access device. The three-fold clip element includes a first portion, a second portion and third portion. The deformable container may be attached to the first portion of the clip element. The second portion of the clip element may be attached to the first portion by a first pivot. The second portion of the clip element is foldable over the first portion of the clip element for removing one or more air bubbles from the deformable container. The third portion is attached to the second portion by a second pivot, and the third portion of the clip element is foldable over the first portion of the clip element for driving fluid out of said chamber. The locking element may be disposed on the first and third portion of the clip element.

Another aspect of the present invention pertains to a method of flushing or administering a fluid to a vascular access device comprising providing a single use pre-filled delivery device as described herein; providing a vascular access device having a proximal end, a distal end and a passageway therethrough, said proximal end having a female luer tip in fluid communication with said passageway; placing said distal end of said vascular access device in a blood vessel of a patient; engaging said male luer tip of said deformable container with said female luer tip of said vascular access device; applying force to said clip element to deform the collapsible container so that said flush solution in said chamber flows through said passageway into said vascular access device; continuing to apply force to the clip element until said distal end of the locking element engages the said proximal end of the locking element; and disengaging said male luer tip of said deformable container from said female luer tip of said vascular access device.

BRIEF DESCRIPTION OF THE DRAWINGS

FIG. 15 is a side view illustrating an eighth embodiment of the single use pre-filled delivery device of the present invention having a tip cap.

FIG. 16 is a side view illustrating an eighth embodiment of the single use pre-filled delivery device of the present invention having a tip cap.

FIG. 17 is a side view illustrating an eighth embodiment of the single use pre-filled delivery device of the present invention having a tip cap.

DETAILED DESCRIPTION OF THE INVENTION

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

The term "deformable" refers to a wall or container that is structured to be flexible enough to collapse at least partially into the inner chamber under manual depression. The shape and extent of the deformation will vary with the various configurations of the inner chamber and deformable container.

As used herein, the term "luer" with respect to a connector, connection or tip refers to a connection collar that is the standard way of attaching syringes, catheters, hubbed needles, IV tubes, etc. to each other. The luer connection consists of male and female interlocking tubes, slightly tapered to hold together better with even just a simple pressure/twist fit. Luer connectors can optionally include an additional outer rim of threading, allowing them to be more secure. The luer connector male end is generally associated with a delivery device and can interlock and connect to the female end located on a vascular access device (VAD). A luer connector comprises a distal end, a proximal end, an irregularly shaped outer wall, a profiled center passageway for fluid communication from the chamber of the barrel of a syringe to the hub of a VAD. A luer connector also has a distal end channel that releasably attaches the luer connector to the hub of a VAD, and a proximal end channel that releasably attaches the luer connector to the barrel of a syringe.

The single use pre-filled delivery device of the present invention is shown in FIGS. 1-7. A single use sterile delivery device of the present invention reduces the risk associated with contamination due to manual filling a syringe with flush solution or medicament from a vial. Generally speaking, the single use device of the present invention capable of delivering sterile solution to the female luer connection of a VAD. In general, the device comprises a deformable container with a male luer connector capable of holding between 0.5 mL and 10 mL of sterile and a clip element that collapses the deformable container to expel the solution within. The deformable container includes a male luer connector that enables secure connection to the female luer connector within a VAD. The clip element contains a pivot which is activated by pressing the moveable sides together to expel the solution from the deformable container.

Figure 1:
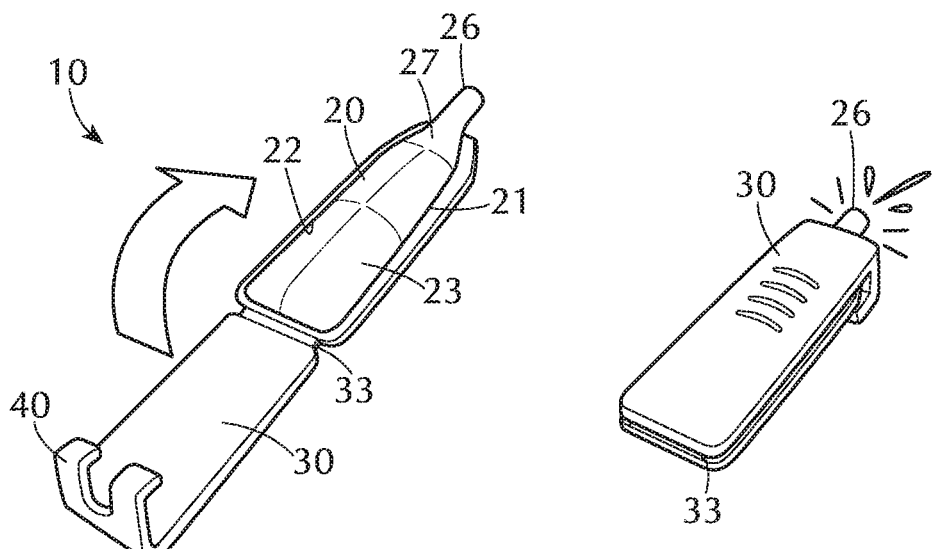
FIG. 1 is a perspective view illustrating one embodiment of the single use pre-filled delivery device of the present invention.

Referring to FIG. 1, a single use pre-filled delivery device 10 according to the present invention generally comprises a deformable container 20 including a side wall 21 having an inside surface 22 defining a chamber 23 for retaining fluid, a clip element 30, and a locking element 40. In operation, delivery device 10 is attached to a patient's catheter via a patient's vascular access device (VAD). The deformable container 20 further comprises a closed proximal end 24 and an open distal end 25 including a male luer tip 26 having a passageway 27 therethrough providing fluid communication with the chamber 23. The male luer tip 26 may be removably connectable to a female luer connection of a vascular access device. Thus, the delivery device of the present invention is capable of a generating a secure connection with a receiving needleless female vascular access connector. The clip element 30 comprises a distal end 31, proximal end 32, and a pivot 33 located between the distal end 31 and the proximal end 32 of the clip element 30 for collapsing the deformable container 20 to drive fluid out of the chamber 23 by movement of the proximal end 32 towards the distal end 31. In one or more embodiments, the pivot 33 may be a hinge, which may be in the form of a living hinge. The deformable container 20 may be attached to the clip element 30. The locking element 40 may be disposed on the clip element 30.

One advantage of the present invention over prior is that the clip element 30 of the present invention improves control of fluid delivery from the deformable container 20.

In one or more embodiments, the single use pre-filled delivery device 10 further includes a tip cap 45 that is releasably connected to the male luer tip 26 of the deformable container 20 for sealing the passageway 27. FIGS. 8-17 show an embodiment of the single use pre-filled delivery device 10 of the present invention having a tip cap 45.

In one or more embodiments, the vascular access device is a syringe, extension set, intravenous set, stop cock, tubing, high pressure extension tubing, or needleless connector.

In one or more embodiments, the single use pre-filled delivery device 10 further includes a pre-selected amount of fluid in the chamber 23. The pre-selected amount of fluid in the chamber 23 may be from 0.5 ml to 10 ml. In one or more embodiments, the fluid may include a flush solution or a medicament. The flush solution may be any solution intended for flushing or maintaining performance of VAD's. The flush solution may be selected from the group consisting of saline flush solution, water, heparin flush solution or a combination thereof. These solutions are known in the art and are readily available. The single-use delivery device 10 is pre-filled with flush solution during or after the assembly of the syringe using sterile filling methods. Such prefilled assemblies may be supplied with a tip cap 45 that seals the passageway 27 of the deformable container 20 and male luer tip 26. The tip cap may be is formed of material selected from a group of thermoplastic materials and elastomeric materials such as natural and synthetic rubber, thermoplastic elastomers, polyolefin, polyester or other injection moldable or formable resin, combinations thereof, or other easily disposable and/or recyclable material. Thermoplastic elastomers include, but are not limited to, polypropylene, polyethylene and the like. Once assembled, the syringe assembly may be used in flushing or administering a fluid to a VAD such as a catheter of an I.V. set.

The locking element 40 of the present invention minimizes, limits or prevents reflux of solution in the passageway 27. The locking element 40 also provides confirmation to the user of solution delivery. In one or more embodiments, the locking element 40 includes at least one protrusion and at least one corresponding cavity. In one or more embodiments, the at least one protrusion is disposed on the proximal end 32 of the clip element 30 and the corresponding cavity is disposed on the distal end 31 of the clip element 30. In another embodiment, the at least one protrusion is disposed on the distal end 31 of the clip element 30 and the at least one corresponding cavity is disposed on the proximal end 32 of the clip element 30. The locking element 40 is arranged to be manually activated by a user after the protrusion engages to the corresponding cavity after the fluid has been expelled from the deformable container 20. When the entire contents of the inner chamber 23 are expelled and the protrusion is in contact and engages with the cavity to locks the proximal end 32 of the clip element 30 to the distal end 31 of the clip element 30.

In one or more alternative embodiments, detents or tabs on the locking element 40 may be used to retain the proximal end 32 of the clip element 30 to the distal end 31 of the clip element 30.

In an alternate embodiment of the present invention, the locking element 40 includes a racheting mechanism having a plurality of teeth and a catch. In one embodiment, the catch is disposed on the proximal end 32 of the clip element 30 and the plurality of teeth is disposed on the distal end 31 of the clip element 30. In another embodiment, the catch is disposed on the distal end 31 of the clip element 30 and the plurality of teeth is disposed on the proximal end 32 of the clip element 30. The locking element 40 is arranged to be manually activated by a user after the catch engages to one or more of the plurality of teeth.

In an alternate embodiment of the present invention, the locking element 40 includes a snap fit element to connect the distal end 31 of the clip element 30 to the proximal end 32 of the clip element 30 upon the release.

In one embodiment, the pivot 33 is positioned on the proximal end 24 of the deformable container 20. In another embodiment, the pivot 33 is positioned on the distal end 25 of the deformable container 20. The pivot 33 may be oriented in a perpendicular position with respect to the distal end 25 of the deformable container 20.

The locking element 40 enables the clip element 30 to be secured in place after the solution has been expelled. The locking element 40 also limits reflux of solution in the fluid path of the vascular access. The locking element 40 provides feedback to the user to confirm delivery of a desired volume of fluid from the chamber 23. The feedback may be tactile, visual or audible.

The materials for the deformable container 20 will have to be chosen based not only on performance but on compatibility with the injectable liquid. In a preferred embodiment the single use pre-filled delivery device 10 is prefilled with injectable liquid. There may be a substantial amount of time between when the delivery device 10 is filled and when the contents of the delivery device 10 are delivered. Accordingly, materials chosen for delivery device 10 may have to be stable under long term storage.

The deformable container 20, clip element 30 and locking element 40 may be made of thermoplastic elastomers, polyolefin, polyester or other injection moldable or formable resin, natural rubber, synthetic rubber, thermoplastic materials, or other easily disposable and/or recyclable material and combinations thereof. Thermoplastic elastomers include, but are not limited to, polypropylene, polyethylene and the like. Materials should be chosen to be compatible with the solution, medicament and manufacturing process being used. It is envisioned that in one or more embodiments, the delivery device of the present invention may be made of a single material to facilitate recycling of the device.

In one or more embodiments, the clip element 30 further includes at least one protrusion for removing one or more air bubbles from the delivery device 10 and controlling the delivery of fluid from the delivery device 10.

Figure 2:
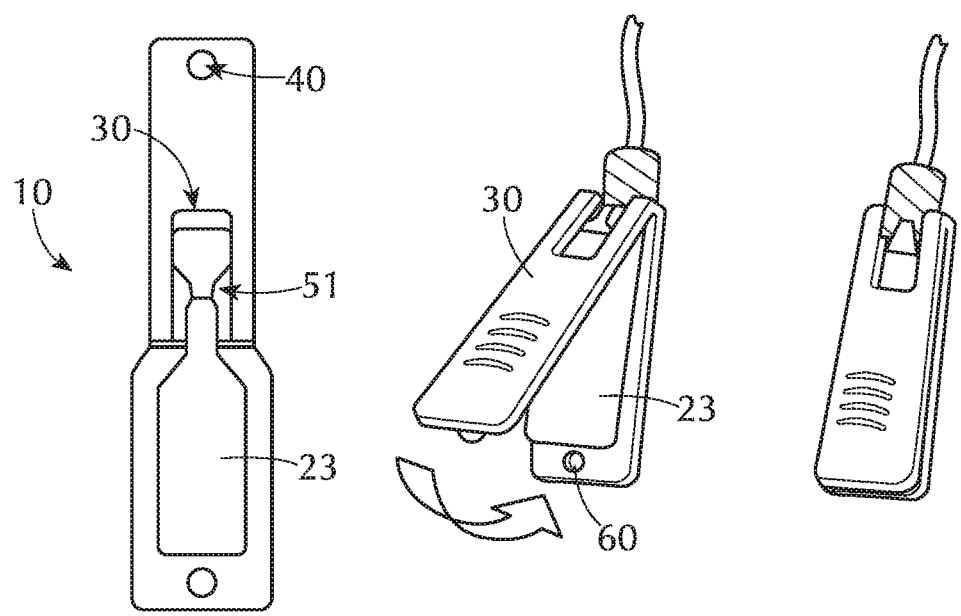
FIG. 2 is a perspective view illustrating a second embodiment of the single use pre-filled delivery device of the present invention.
Figure 3:
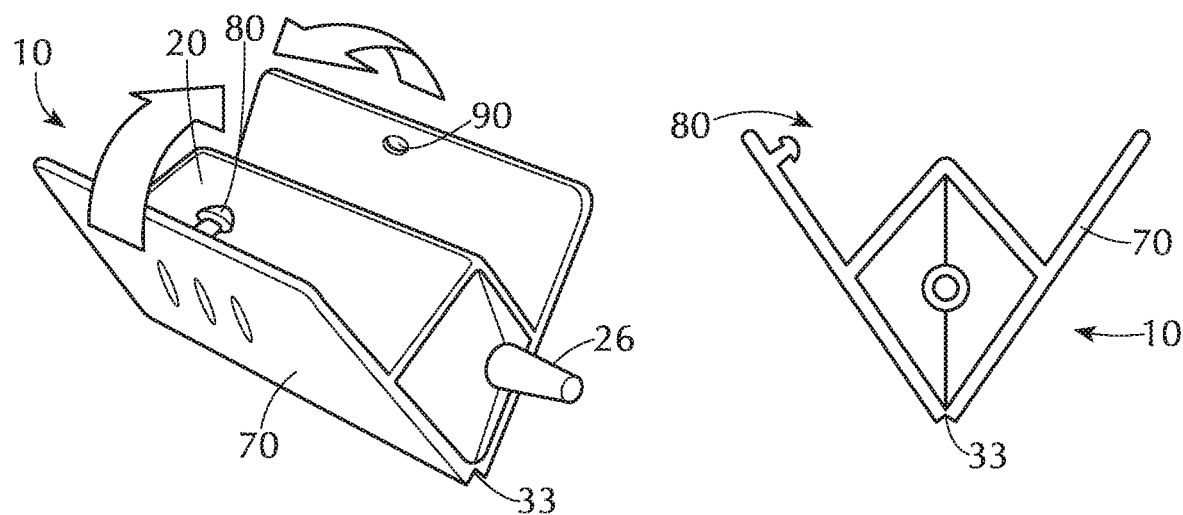
FIG. 3 is a perspective view illustrating a third embodiment of the single use pre-filled delivery device of the present invention.
Figure 4:
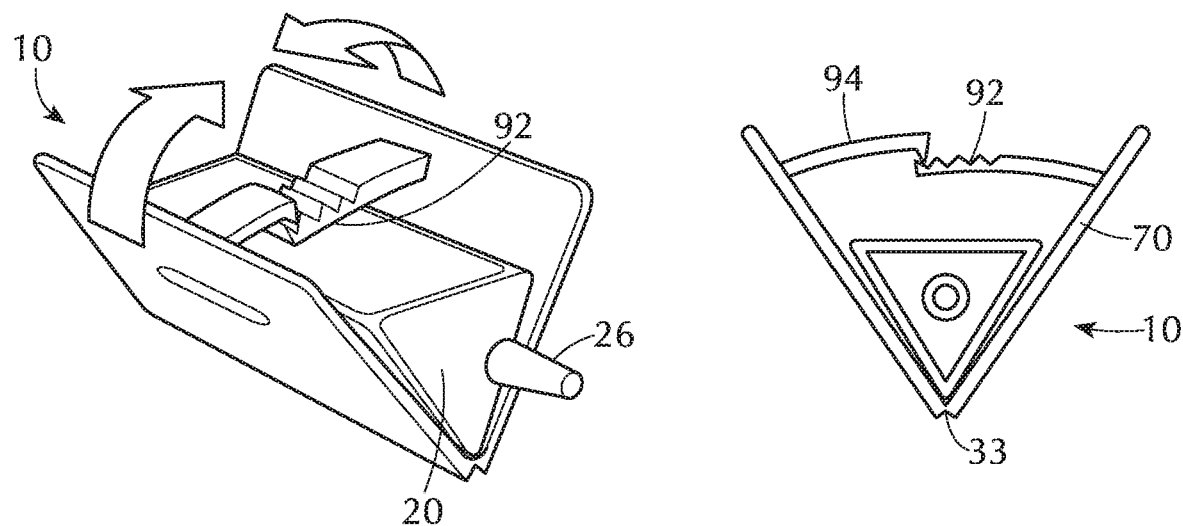
FIG. 4 is a perspective view illustrating a fourth embodiment of the single use pre-filled delivery device of the present invention.
Figure 5:
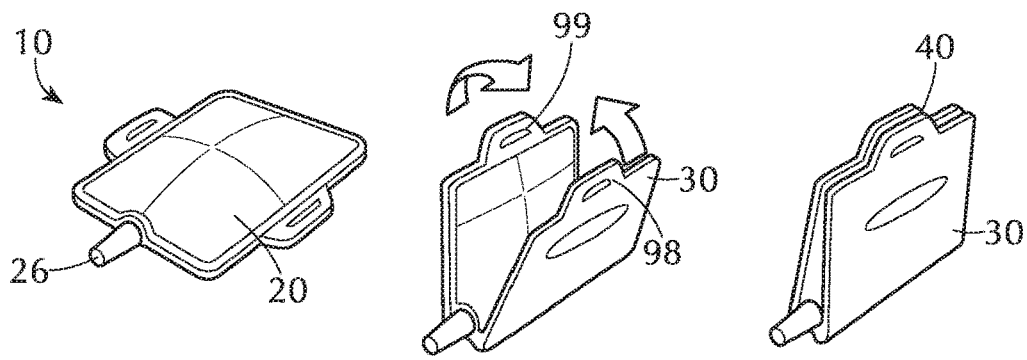
FIG. 5 is a perspective view illustrating a fifth embodiment of the single use pre-filled delivery device of the present invention.

There are several embodiments of the orientation of the clip element 30. As shown in FIG. 1, the delivery device 10 comprises one pivot 33 positioned opposite of the male luer tip of the deformable container 20 between the proximal end and distal end of the clip element 30. As shown in FIG. 1, the delivery device 10 comprises a locking element 60 having a forked tip on the proximal end of the clip element which engages the distal end of the clip element near the male luer tip upon activation. As shown in FIG. 2, the delivery device 10 comprises a V-shaped clip element having one pivot 33 positioned mid-way along the clip element near of the male luer tip of the deformable container 20. The delivery device 10 may include a frangible seal 51 to close the passageway of the chamber 23. As shown in FIG. 2, the delivery device 10 comprises a locking element 40 having a protrusion on the distal end of the clip element which engages a cavity on the proximal end of the clip element. As shown in FIGS. 3-5, the delivery device comprises a deformable container positioned in between a V-shaped clip element, said V-shaped clip element comprising two flat longitudinal surfaces 70 connected by pivot 33 positioned perpendicular to the male luer tip located on the distal end of the deformable container. As shown in FIG. 3, in one embodiment, the locking element includes a protrusion 80 on one longitudinal end of the clip element which engages a corresponding cavity 90 located on the opposite end of the clip element. As shown in FIG. 4, in one embodiment, the locking element includes a plurality of teeth 92 on one longitudinal end of the clip element which engages a corresponding catch 94 located on the opposite end of the clip element. As shown in FIG. 5, in one embodiment, the locking element includes detents or a tab 98 on one longitudinal end of the clip element which engages a corresponding slot or cavity 99 located on the opposite end of the clip element. The embodiments of FIGS. 1-5 are activated by pressing the moveable distal and proximal ends of the clip element together to activate the device and deliver the contents.

Figure 6:
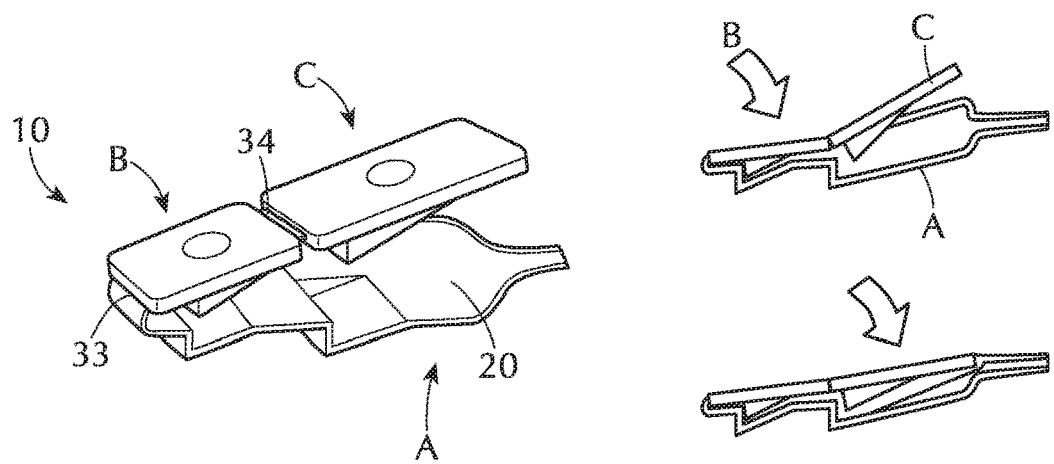
FIG. 6 is a perspective view illustrating a sixth embodiment of the single use pre-filled delivery device of the present invention.

As shown in FIG. 6, the delivery device 10 comprises two pivots 33 and 34 to create a three-fold clip element comprising portions a first portion A, a second portion B and third portion C. Pivot 33 connects portions A and B. Pivot 34 connects portions B and C. Deformable container 20 is attached to portion A. Upon activation, portion B folds upon the proximal end of portion A via pivot 33 to serve a priming function for the removal of air bubbles from deformable container 20. In particular, as shown in FIG. 6, the second portion B compresses the deformable container 20 by squeezing the deformable container 20 between the first portion A and second portion B. Portion C folds upon portion A via pivot 34 for the expulsion of fluid from deformable container 20.

Figure 7:
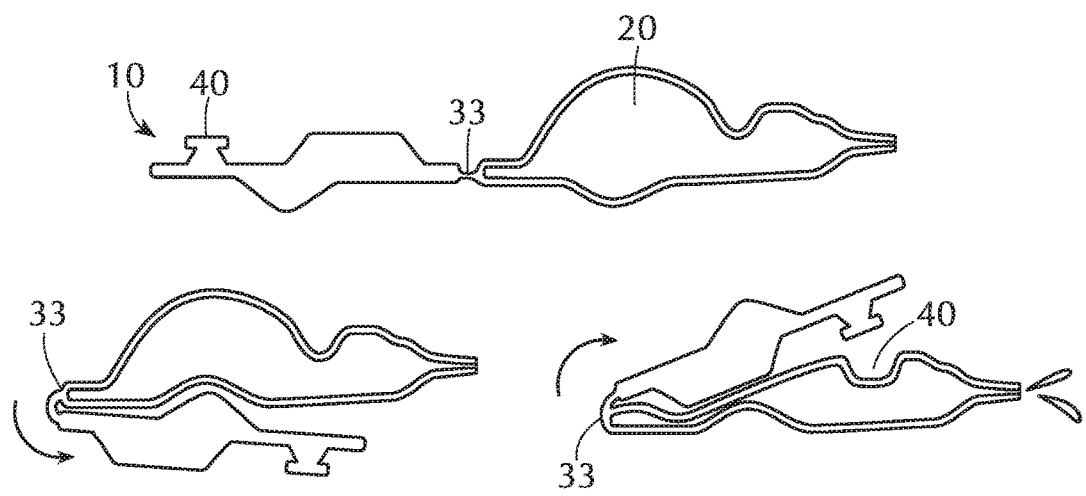
FIG. 7 is a perspective view illustrating a seventh embodiment of the single use pre-filled delivery device of the present invention.
Figure 8:
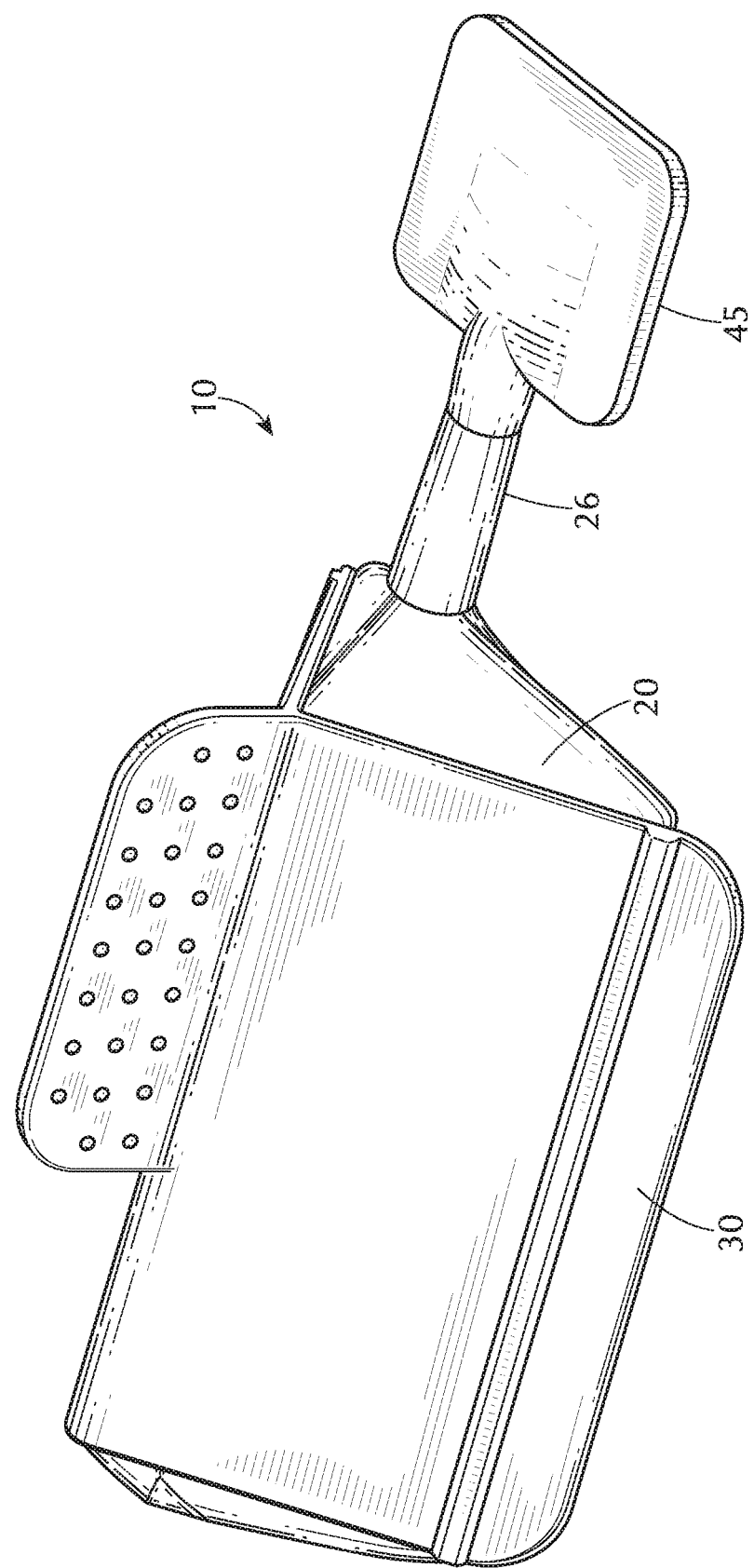
FIG. 8 is a perspective view illustrating an eighth embodiment of the single use pre-filled delivery device of the present invention having a tip cap.
Figure 9:
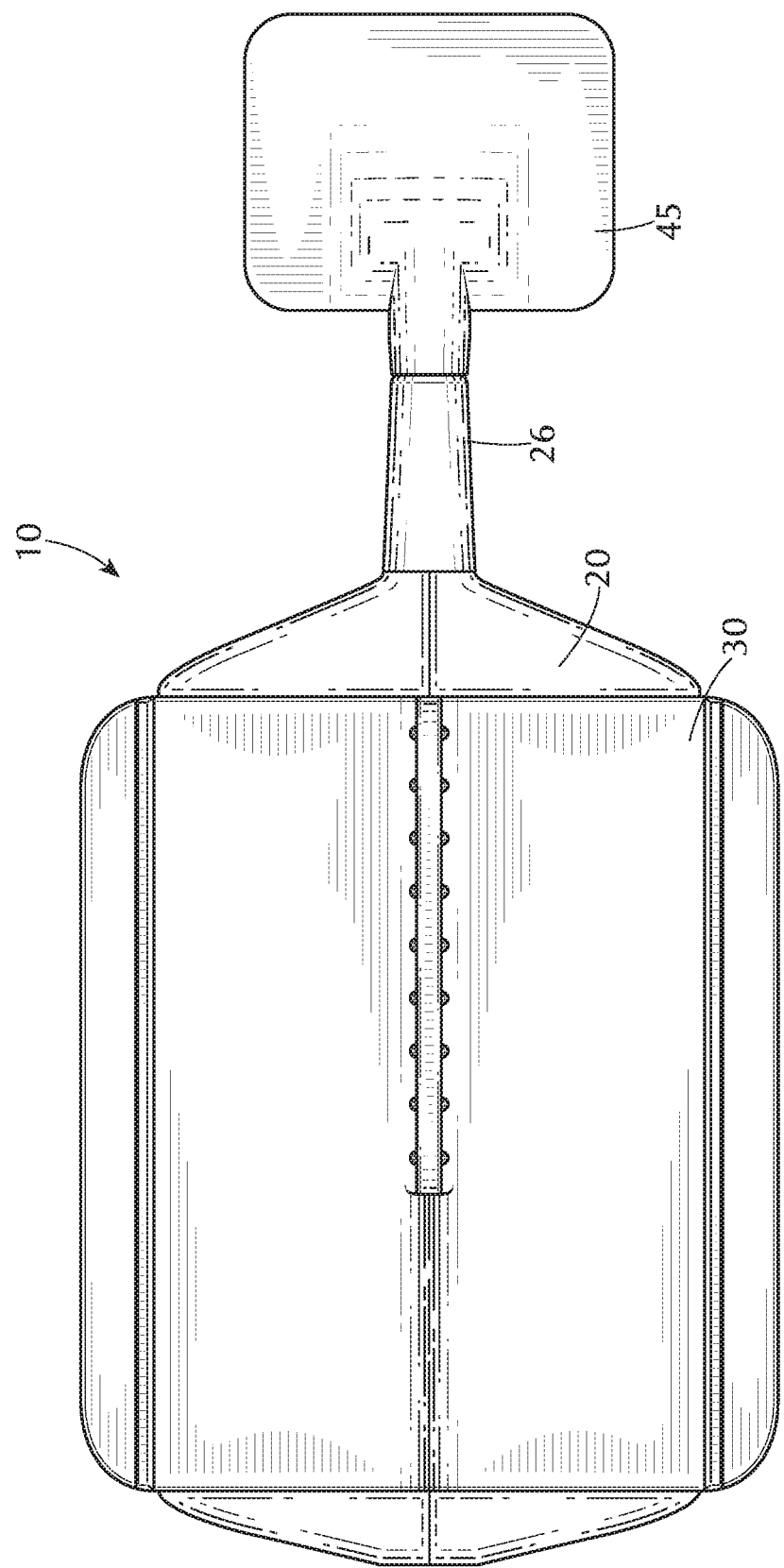
FIG. 9 is a top view illustrating an eighth embodiment of the single use pre-filled delivery device of the present invention having a tip cap.
Figure 10:
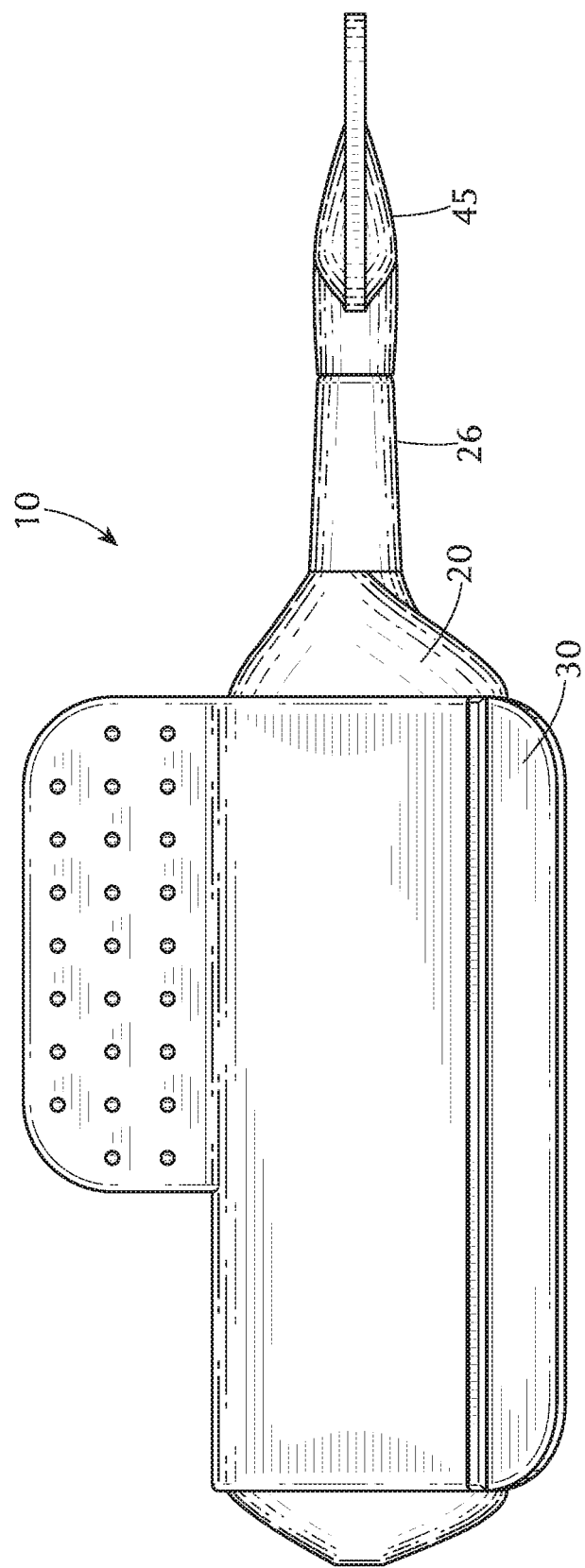
FIG. 10 is a right side view illustrating an eighth embodiment of the single use pre-filled delivery device of the present invention having a tip cap.
Figure 11:
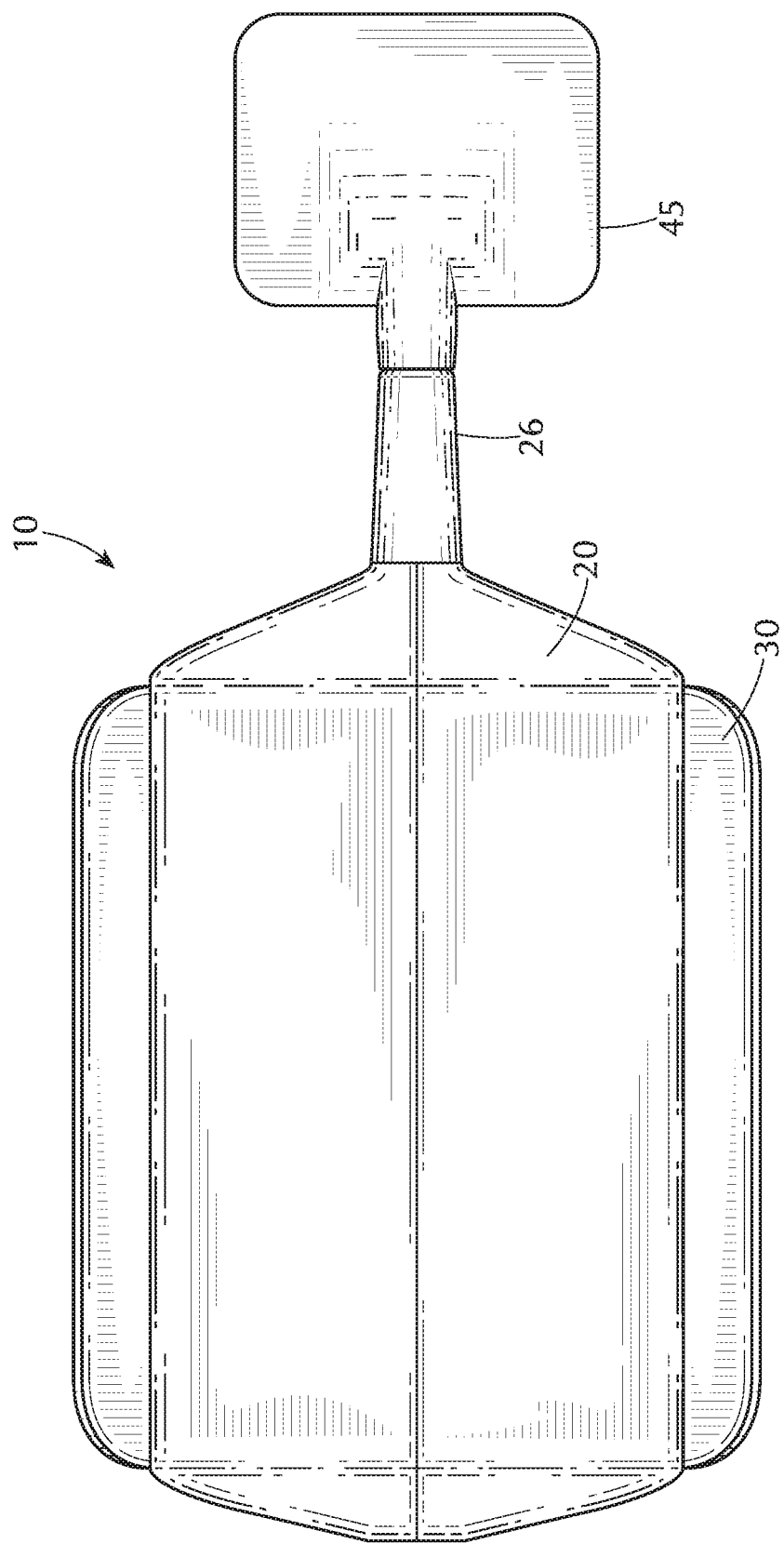
FIG. 11 is a bottom view illustrating an eighth embodiment of the single use pre-filled delivery device of the present invention having a tip cap.
Figure 12:
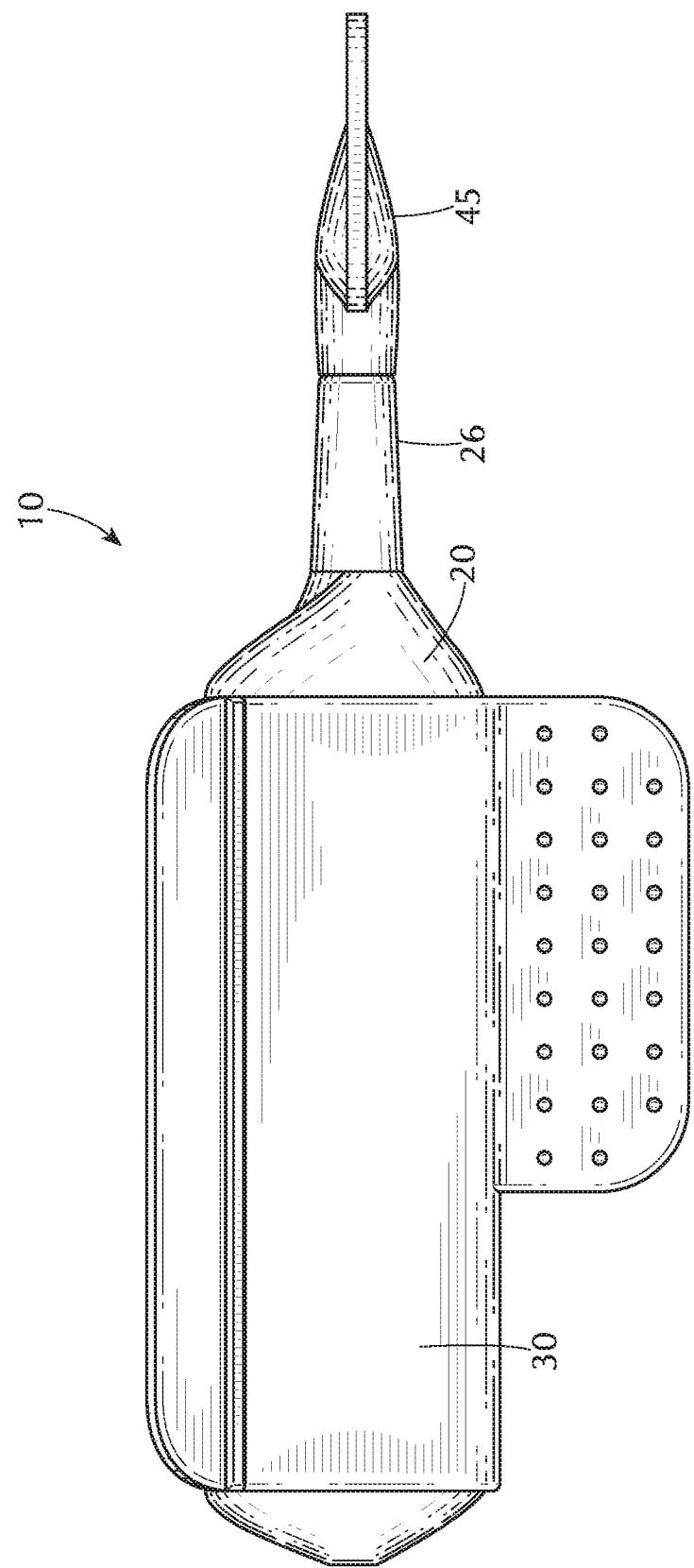
FIG. 12 is a side view illustrating an eighth embodiment of the single use pre-filled delivery device of the present invention having a tip cap.
Figure 14:
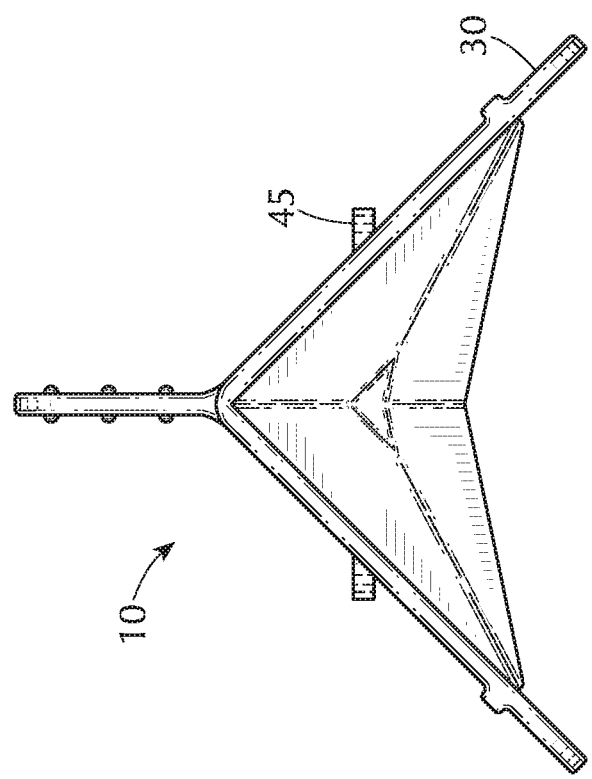
FIG. 14 is a front view illustrating an eighth embodiment of the single use pre-filled delivery device of the present invention having a tip cap.
Figure 13:
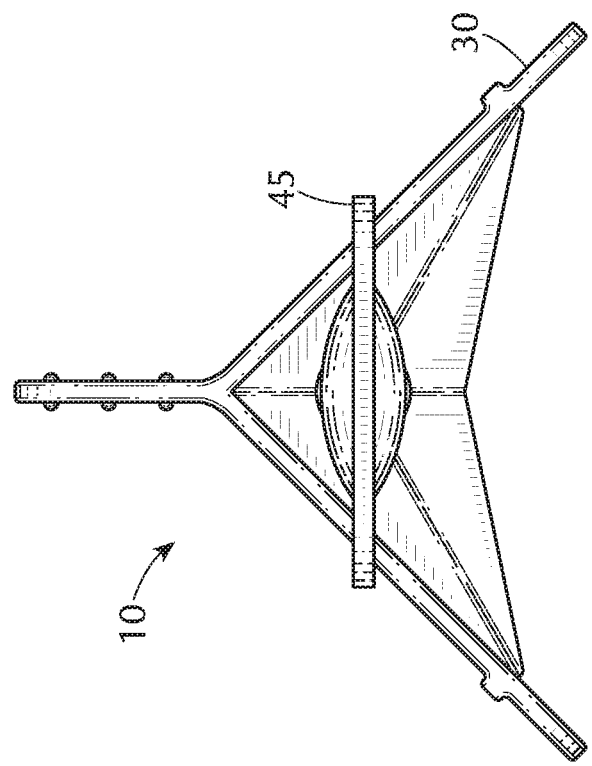
FIG. 13 is a back view illustrating an eighth embodiment of the single use pre-filled delivery device of the present invention having a tip cap.

As shown in FIG. 7, the delivery device 10 comprises one pivot 33 to create a two-fold clip element comprising portions A and B. Pivot 33 allows movement in an axial direction in a clockwise or counter-clockwise direction. When portion A moves along pivot 33 in a counter-clockwise direction, portion A serves a priming function for the removal of air bubbles from deformable container 20. When portion A moves along pivot 33 in a clockwise direction, portion A of clip element serves to expel fluid from deformable container 20. As shown in FIG. 7, locking element 40 is in the form of a detent or tab which engages a recess 41.

Additional embodiments are possible in which the clip element 30 of the device includes features which allow for additional control of the volume and rate of fluid expelled from the device. In one embodiment, the moveable clip element contains protrusions, which control the delivery of solution volume for priming the syringe for use and delivery of the remaining solution. The term "priming" is defined as the removal of the air bubble. Two additional embodiments include an embodiment with the protrusion on one side of the clip, as shown in FIG. 6, and on both sides of the clip elements, as shown in FIG. 7.

In an alternate embodiment, single use pre-filled delivery device 10 comprises a deformable container including a side wall having an inside surface defining a chamber for retaining fluid, a closed proximal end and an open distal end including a male luer tip having a passageway therethrough providing fluid communication with said chamber, a three-fold clip element and a locking element. The male luer tip is removably connectable to a female luer connection of a vascular access device. The three-fold clip element includes a first portion, a second portion and third portion. The deformable container may be attached to the first portion of the clip element. The second portion of the clip element may be attached to the first portion by a first pivot. The second portion of the clip element is foldable over the first portion of the clip element for removing one or more air bubbles from the deformable container. The third portion is attached to the second portion by a second pivot, and the third portion of the clip element is foldable over the first portion of the clip element for driving fluid out of said chamber. The locking element may be disposed on the first and third portion of the clip element.

The delivery device 10 of the present invention may be used in conjunction with a vascular access device having a proximal end, a distal end and a passageway 27 therethrough, said proximal end having a female luer tip in fluid communication with said passageway 27. To use the delivery device 10 in a flushing procedure or to administering a fluid, the user engages the male luer tip 26 of the deformable container 20 of the delivery device 10 with the female luer tip of a vascular access device, after the distal end of said vascular access device has been placed in a blood vessel of a patient. The user then applies force to the clip element 30 to deform the collapsible container 20 so that said flush solution in said chamber 23 flows through said passageway 27 into said vascular access device. The user continues to apply force to the clip element 30 until said distal end 41 of the locking element 40 engages the said proximal end 42 of the locking element 40. After the expulsion of the desired amount of fluid from the chamber 23, the user disengages said male luer tip 26 of said deformable container 20 from said female luer tip of said vascular access device. One advantage of the present invention is that the delivery device of the present invention collapses to a configuration with minimal dead space and secures using the locking element 40. Another advantage of the present invention is that the moveable clip element 30 allows the user to sense the resistance in the fluid path, wherein increased resistance could allow the operator to detect resistance within the components of the delivery device or vascular access device.

The device of the present invention may be produced as a single component or as multiple parts assembled in a second step. As a single component, the clip element 30, deformable container 20 and locking element 40 are incorporated into a single part. In the multiple component configuration, the clip element 30, deformable container 20 and locking element 40 may be formed from any number of individual parts and assembled together.

The single use pre-filled delivery device 10 of the present invention may be manufactured in accordance with a blow-fill-seal technique of a character well understood by those skilled in the art.

The concept of a blow-fill-seal process is that a container is formed, filled, and sealed as a unitary container in a continuous manner without human intervention in a sterile, enclosed area inside a machine. Blow-fill-seal manufacturing forms a closed container by extruding and forming a parison within a mold, filling the container and sealing the container in a single step. This manufacturing process enables the device to be produced in a single process. For example, pharmaceutical grade resin is extruded into a tube, which is then formed into a container. A mandrel is inserted into the newly formed container and filled. The container is then sealed, all inside a sterile, shrouded chamber. The product is then discharged to a non-sterile area for packaging and distribution. This blow-fill-seal technique comprises the continuous extrusion through an extruder head of a length of a parison in the form of a hollow tube between and through two co-acting first or main mold halves. The method includes the step of cutting off the parison below the extruder head and above the main mold halves to create an opening which allows a blowing and filling nozzle assembly to be moved downwardly into the opening in the parison for molding and thereafter filling a molded container. When the container portion of the container assembly is filled with the desired amount of liquid, the blowing and filling nozzle assembly is retracted from the opening in the parison. A separate pair of co-acting second or upper sealing mold halves are then moved together around the exposed length of parison to form and seal the container upper portion. The finished container assembly, completely formed, filled, and sealed as a unitary structure is then conveyed out of the molding apparatus.

A single use, pre-filled, sterile delivery device of the present invention reduces the risk associated with contamination due to manual filling a syringe with flush solution or medicament from a vial.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A single use pre-filled delivery device comprising:
   a deformable container including a side wall having an inside surface defining a chamber for retaining fluid, a closed proximal end and an open distal end including a male luer tip having a passageway therethrough providing fluid communication with the chamber, the male luer tip —removably connectable to a female luer connection of a vascular access device; and
   a three-fold clip element having a first portion, a second portion and a third portion, the first portion having a proximal end and a distal end,
   the deformable container being attached to the first portion of the clip element,
   the second portion being attached to the first portion by a first pivot, the second portion of the clip element being foldable over the first portion of the clip element to fold upon the proximal end of the first portion to remove one or more air bubbles from the deformable container, wherein the second portion compresses the deformable container by squeezing the deformable container between the first portion and the second portion;

the third portion being attached to the second portion by a second pivot, the third portion of the clip element being foldable over the first portion of the clip element to drive the fluid out of the chamber; wherein the clip element further includes at least one protrusion on one side of the clip element and configured to control the volume and rate of fluid expelled from the deformable container; the at least one protrusion comprising a first protrusion on the second portion to remove the one or more air bubbles from the deformable container; and wherein the at least one protrusion further comprises a second protrusion on the third portion to expel the fluid from the deformable container.

2. The single use pre-filled delivery device of claim 1, wherein the vascular access device is a syringe, extension set, intravenous set, stop cock, tubing, high pressure extension tubing, or needleless connector.

3. The single use pre-filled delivery device of claim 1, further comprising a pre-selected amount of the fluid in the chamber.

4. The single use pre-filled delivery device of claim 3, wherein the fluid comprises a sterile flush solution.

5. The single use pre-filled delivery device of claim 4, wherein the sterile flush solution is saline, heparin, water or a combination thereof.

6. The single use pre-filled delivery device of claim 4, wherein the fluid comprises a medicament or drug.

7. The single use pre-filled delivery device of claim 3, wherein the pre-selected amount of the fluid in the chamber is from 0.5 ml to 10 ml.

8. The single use pre-filled delivery device of claim 1, wherein the deformable container is made of thermoplastic elastomers, polyolefin, polyester or other injection moldable or formable resin.

9. The single use pre-filled delivery device of claim 1, further comprising a tip cap releasably connected to the male luer tip.

10. A method of administering a fluid to a vascular access device comprising the steps of:
  (a) providing a single use pre-filled delivery device of claim 1; the female luer connection of the vascular access device;
  (c) folding the second portion of the clip element over the first portion of the clip element to remove the one or more air bubbles from the deformable container;
  (d) folding the third portion of the clip element over the first portion of the clip element to drive fluid out of the chamber; and
  (e) disengaging the male luer tip of the deformable container from the the female luer connection of the vascular access device.

* * * * *